(12) United States Patent
Wu et al.

(10) Patent No.: US 9,775,936 B2
(45) Date of Patent: Oct. 3, 2017

(54) BLOOD PUMP WITH SEPARATE MIXED-FLOW AND AXIAL-FLOW IMPELLER STAGES, COMPONENTS THEREFOR AND RELATED METHODS

(75) Inventors: Jingchun Wu, Irvine, CA (US); Josiah Verkaik, Lompoc, CA (US)

(73) Assignee: WorldHeart Corp., Miami Lakes, FL (US)

( * ) Notice: Subject to any disclaimer, the term of this patent is extended or adjusted under 35 U.S.C. 154(b) by 1211 days.

(21) Appl. No.: 13/275,912

(22) Filed: Oct. 18, 2011

(65) Prior Publication Data

US 2012/0134793 A1    May 31, 2012

Related U.S. Application Data

(60) Provisional application No. 61/394,213, filed on Oct. 18, 2010, provisional application No. 61/394,220, filed on Oct. 18, 2010.

(51) Int. Cl.
*A61M 1/10* (2006.01)
*A61M 1/12* (2006.01)
*F04D 3/00* (2006.01)

(52) U.S. Cl.
CPC ............ *A61M 1/101* (2013.01); *A61M 1/125* (2014.02); *F04D 3/00* (2013.01); *Y10T 29/49245* (2015.01)

(58) Field of Classification Search
CPC .............................. A61M 1/125; A61M 1/101
See application file for complete search history.

(56) References Cited

U.S. PATENT DOCUMENTS

| 4,625,712 | A | * | 12/1986 | Wampler ...................... 600/16 |
| 4,846,152 | A | * | 7/1989 | Wampler et al. ............... 600/16 |
| 4,850,796 | A | | 7/1989 | Miller |
| 4,944,722 | A | | 7/1990 | Carriker et al. |
| 5,376,114 | A | | 12/1994 | Jarvik |
| 5,678,306 | A | | 10/1997 | Bozeman et al. |

(Continued)

FOREIGN PATENT DOCUMENTS

| WO | 94/09274 | 4/1994 |
| WO | 2005030296 | 4/2005 |

(Continued)

OTHER PUBLICATIONS

PCT International Search Report for International Patent Application No. PCT/US2011/056722 dated Jan. 23, 2012 (5 pages).

(Continued)

*Primary Examiner* — Woody Lee, Jr.
(74) *Attorney, Agent, or Firm* — Christopher & Weisberg, P.A.

(57) ABSTRACT

A rotordynamic pump for delivering continuous flow of fluids, such as blood, is provided. In one embodiment, the pump includes a stator housing having an inlet and an outlet. A rotor hub is disposed within the stator housing having a first, mixed-stage impeller and a second, axial-flow stage impellers. One or more stator vanes and extend radially inwardly from the stator housing. In one particular embodiment, the second stage impeller is disposed nearer to the outlet than to the inlet. The stator vanes may include a first set of stator vanes disposed between the first and second stage impellers, and a second set of stator vanes positioned between the second stage impellers and the outlet.

15 Claims, 11 Drawing Sheets

(56) References Cited

U.S. PATENT DOCUMENTS

| | | |
|---|---|---|
| 5,695,471 A | 12/1997 | Wampler |
| 5,755,784 A | 5/1998 | Jarvik |
| 5,776,190 A | 7/1998 | Jarvik |
| 5,824,070 A | 10/1998 | Jarvik |
| 5,851,174 A * | 12/1998 | Jarvik et al. .................. 600/16 |
| 5,888,241 A | 3/1999 | Jarvik |
| 5,911,685 A | 6/1999 | Siess et al. |
| 5,965,089 A | 10/1999 | Jarvik et al. |
| 6,146,325 A | 11/2000 | Lewis et al. |
| 6,176,822 B1 | 1/2001 | Nix et al. |
| 6,200,260 B1 | 3/2001 | Bolling |
| 6,227,820 B1 | 5/2001 | Jarvik |
| 6,244,835 B1 | 6/2001 | Antaki et al. |
| 6,344,022 B1 | 2/2002 | Jarvik |
| 6,387,037 B1 | 5/2002 | Bolling et al. |
| 6,390,969 B1 | 5/2002 | Bolling et al. |
| 6,395,026 B1 | 5/2002 | Aboul-Hosn et al. |
| 6,428,464 B1 | 8/2002 | Bolling |
| 6,447,266 B2 | 9/2002 | Antaki et al. |
| 6,530,876 B1 | 3/2003 | Spence |
| 6,532,964 B2 | 3/2003 | Aboul-Hosn et al. |
| 6,610,004 B2 | 8/2003 | Viole et al. |
| 6,685,621 B2 | 2/2004 | Bolling et al. |
| 6,716,189 B1 | 4/2004 | Jarvik et al. |
| 6,719,791 B1 * | 4/2004 | Nusser et al. .............. 623/3.13 |
| 6,761,532 B2 | 7/2004 | Capone et al. |
| 6,889,082 B2 | 5/2005 | Bolling et al. |
| 7,005,080 B2 | 2/2006 | Holland et al. |
| 7,070,398 B2 * | 7/2006 | Olsen et al. .................. 417/353 |
| 7,144,364 B2 | 12/2006 | Barbut et al. |
| 7,238,151 B2 | 7/2007 | Frazier |
| 7,264,606 B2 | 9/2007 | Jarvik et al. |
| 7,381,179 B2 | 6/2008 | Aboul-Hosn et al. |
| 7,435,059 B2 | 10/2008 | Smith et al. |
| 7,458,929 B2 | 12/2008 | Bolling et al. |
| 7,468,050 B1 | 12/2008 | Kantrowitz |
| 7,479,102 B2 | 1/2009 | Jarvik |
| 7,544,160 B2 | 6/2009 | Gross |
| 7,585,322 B2 | 9/2009 | Azzolina |
| 7,614,997 B2 | 11/2009 | Bolling |
| 2003/0021683 A1 | 1/2003 | Capone et al. |
| 2003/0139643 A1 | 7/2003 | Smith et al. |
| 2003/0228214 A1 * | 12/2003 | McBride ....................... 415/191 |
| 2006/0029495 A1 | 2/2006 | Ishii et al. |
| 2007/0253842 A1 | 11/2007 | Horvath et al. |
| 2009/0203957 A1 | 8/2009 | Larose et al. |
| 2011/0237863 A1 | 9/2011 | Ricci et al. |
| 2011/0238172 A1 | 9/2011 | Akdis |
| 2012/0003086 A1 * | 1/2012 | Morris et al. ................ 415/200 |
| 2012/0134793 A1 | 5/2012 | Wu et al. |
| 2012/0134832 A1 | 5/2012 | Wu |

FOREIGN PATENT DOCUMENTS

| | | |
|---|---|---|
| WO | 2010036815 A2 | 4/2010 |
| WO | 2012054435 A1 | 4/2012 |
| WO | 2012054490 A1 | 4/2012 |

OTHER PUBLICATIONS

PCT International Search Report for International Patent Application No. PCT/US2011/56646 dated Jan. 27, 2012 (5 pages).

* cited by examiner

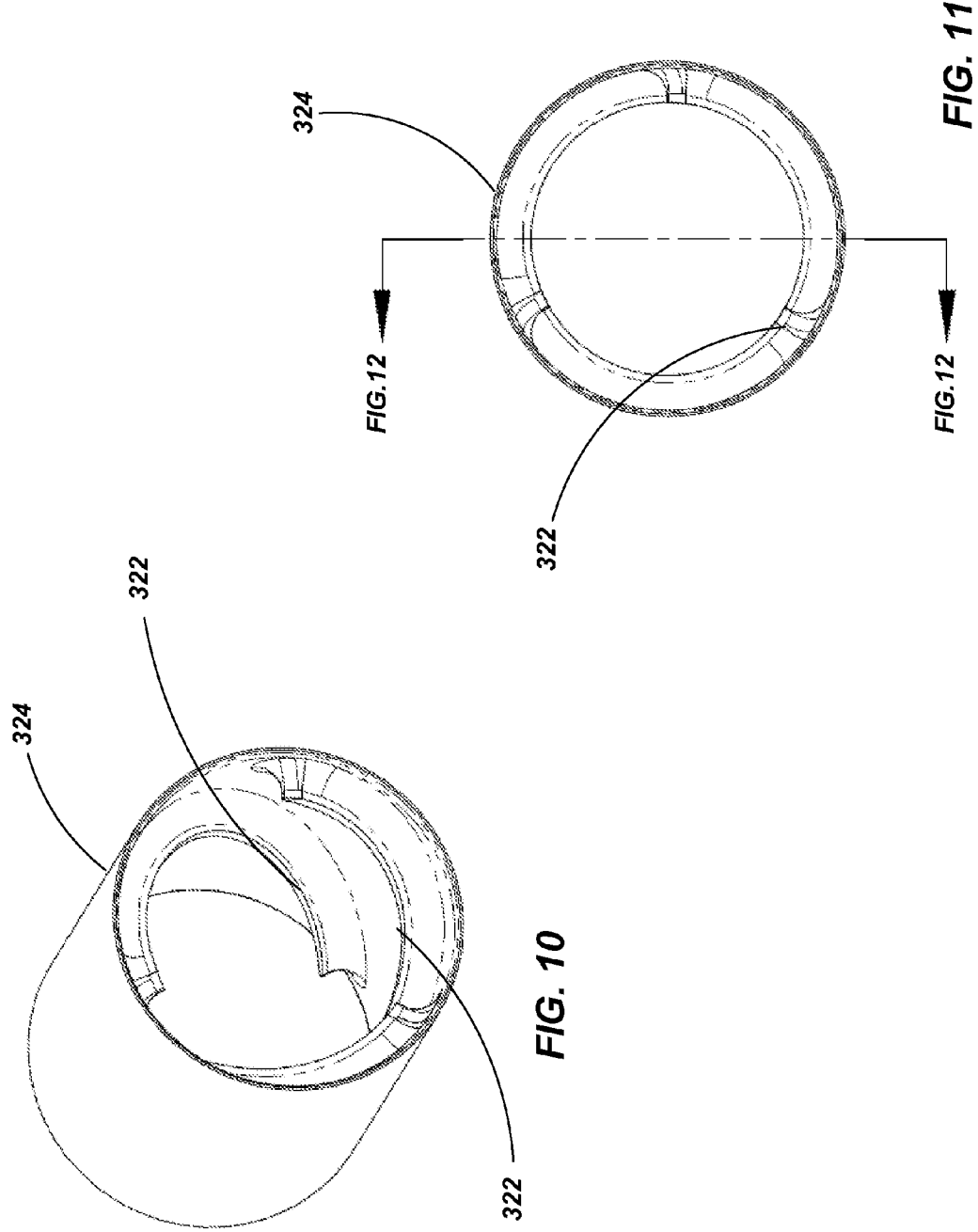

BLOOD PUMP WITH SEPARATE MIXED-FLOW AND AXIAL-FLOW IMPELLER STAGES, COMPONENTS THEREFOR AND RELATED METHODS

CROSS-REFERENCE TO RELATED APPLICATIONS

This application claims priority to U.S. Provisional Patent Application No. 61/394,213 filed Oct. 18, 2010, entitled BLOOD PUMP WITH SEPARATE MIXED-FLOW AND AXIAL FLOW IMPELLER STAGES. This application also claims priority to U.S. Provisional Patent Application No. 61/394,220, filed Oct. 18, 2010, entitled BLOOD PUMP WITH SPLITTER IMPELLER BLADES AND SPLITTER STATOR BLADES. The disclosures of the above-referenced priority applications are incorporated by reference herein in their entireties.

TECHNICAL FIELD

This invention relates generally to pumps. More specifically, this invention relates to blood pumps, such as cardiac assist pumps that may be implanted in a patient.

BACKGROUND OF THE INVENTION

Rotordynamic pumps, such as centrifugal, mixed-flow, and axial-flow pumps with mechanical bearings or magnetically suspended systems, have been widely used as a ventricular assist devices to support patients with heart diseases. In magnetically levitated blood pumps, which generally include an impeller that is both magnetically suspended and rotated without mechanical means, an annular gap located between the rotor and stator suspension and drive components is conventionally designed to be relatively small. A narrow annular flow gap generally necessitates higher rotational speeds of the rotor in order to generate the desired pressure rise and flow rates needed to support patients. One adverse outcome of operating a rotor at high rotational speeds is a tendency for high turbulence flow characteristics within the blood (e.g., high shear stress) that increase the extent and rate of red blood cell damage.

Additionally, for centrifugal or mixed-flow blood pumps with shrouded impellers (i.e., a circumferentially revolved surface interconnecting the impeller blade tips), the fluid within the clearance space between a rotating front shroud and the stationary housing demonstrates a complex three-dimensional structure, leading to retrograde leakage flow and strong disk friction loss. The combination of disk friction loss and the strong vortical flow not only lowers pump efficiency but also potentially induces hemolysis and thrombosis. A similar flow pattern can also occur at the back clearance space between a rotating back shroud and the stationary housing for centrifugal or mixed flow pumps with or without a front shroud. The level of shear stress within the clearance between the walls of a shroud and housing depends, at least in part, on the pump rotational speed.

For centrifugal or mixed-flow blood pumps with unshrouded or semi-open impellers, the lack of a front shroud introduces a problem due to the blade tip leakage flow from pressure-side to suction-side of the blades which occurs through the clearance between the rotating blade tip and the stationary housing. The leakage flow can also generate a jet leakage vortex that interacts with the primary flow, causing hydraulic loss and possibly inducing blood trauma. The shear stress exhibited in the gap or clearance between the blade tip gap and the stationary housing is very sensitive to the pump rotational speed as well as the magnitude of the gap itself.

For axial flow blood pumps with completely magnetically suspended systems, the annular gap located between the cylindrical rotor and housing has to be small enough to maintain the magnetic radial stiffness. Additionally, the axial length of the rotor has to be sized to maintain proper stability, exhibiting sufficient axial stiffness and little yaw. Such an arrangement generally leads to the requirement for high pump speed in order to generate the required pressure rise and flow rate for patients. However, the shear stress exhibited by the fluid within the annular gap region can become very high due to the high rotational speed and the narrowness of the gap. Moreover, conventional designs of axial blood pumps tend to have very long blade profiles (i.e., extending long axial distances and having very large blade wrap angle) and large trailing edge angles (i.e., $\beta_2$ close to 90 degrees). Such a design with very long blade profiles not only increases the blade tip areas with higher shear stress but also leads to flow separation and vortices, particularly at the off-design conditions. Moreover, in addition to deterioration of the pump efficiency, such a design most likely causes undesirable blood damage.

SUMMARY OF THE INVENTION

Various embodiments of rotordynamic pumps for fluids are set forth herein in accordance with the present invention.

In accordance with one embodiment a pump configured to provide continuous fluid flow is provided. The pump comprises a stator housing having an inlet and an outlet. A rotor hub is disposed within the fluid pathway between the inlet and the outlet. The rotor hub comprises a body having a leading portion positioned adjacent the inlet, a trailing portion positioned adjacent the outlet, at least one first-stage impeller blade positioned at the leading portion, at least one second-stage impeller blade positioned between the leading portion and the trailing portion. At least one stator vane extends radially inwardly from the stator housing and is positioned between the inlet and outlet.

In one embodiment, the rotor hub is positioned within the stator housing to define a substantially annular flow path along a length of the rotor hub. The rotor hub may be substantially cylindrical with conical geometries along the leading portion and the trailing portion.

In one embodiment, the first-stage impeller blade is configured as a mixed-flow impeller blade and the second-stage impeller blade is configured as an axial-flow impeller blade.

In one embodiment, the second-stage impeller blade is positioned closer to the inlet than to the outlet. In such an embodiment, the at least one stator vane may be disposed adjacent the at least one second-stage impeller blade and extend to a location adjacent the trailing portion of the rotor hub.

In another embodiment, the second-stage impeller blade is positioned closer to the outlet than to the inlet. In such an embodiment, the at least one stator vane may include at least a first stator vane disposed axially between the at least one second-stage impeller blade and the outlet. Another stator vane may be disposed axially between the at least one first-stage impeller blade and the at least one second-stage impeller blade.

In one embodiment, the at least one stator vane is integrally formed with the with the stator housing. In another embodiment, the at least one stator vane is formed on a tubular insert disposed within the stator housing.

In one embodiment, the rotor hub is configured to be magnetically suspended and rotated by stator during operation of the pump.

In accordance with another embodiment of the present invention, a method of manufacturing a pump is provided. The method comprises providing a stator housing having an inlet and an outlet; providing a rotor hub having a first, mixed-flow stage impeller near a leading portion of the rotor hub and a second, axial-flow stage impeller positioned downstream of the first, mixed flow stage; positioning the rotor hub within the stator housing to define an annular flow path through the stator housing; and providing at least one stator vane extending from the stator housing.

In exemplary embodiments, there are provided a rotordynamic apparatus and method suitable long-term implantation into humans for artificial circulatory support.

In one embodiment, there be provided a rotordynamic blood pump and method comprising a flow path geometry characterized with high hydraulic efficiency, low power consumption, uniform flow fields, and low blood damage.

In another embodiment, there may be provided a rotordynamic blood pump suitable for easy arrangements of magnetic suspension and drive components along the annular portion of the flow path.

Exemplary embodiments may provide an apparatus and method for a multistage fluid pump for pumping bloods and other fluids, which integrates an impeller having at least two stages of blades, with a stator having at least one stage of vanes between axial inlet and axial outlet ports. The first impeller stage includes a high-specific speed centrifugal or mixed-flow impeller region, which may include shrouded or unshrouded blades on the inlet transitional conical region of the rotor. The second and any later impeller stages are within the annulus and are of an axial-flow type impeller region without a shroud. A stator vane stage may be positioned along on outflow transitional conical region of the stator.

High efficiency, low blood damage, and small compact size are often desirable features for a long-term implantable blood pump. High efficiency is provided by the present invention due to the two stage impeller blades. Fluid is directed through the first stage rotating mixed-flow type impeller to gain both kinetic energy and pressure rise and then further to gain kinetic energy and pressure rise from passage through second rotating axial impeller region, thus yielding a total higher head (i.e., pressure rise) at the same pump speed than the pure single stage mixed-flow or single axial flow configuration thus resulting in increased pump efficiency. The higher efficiency provides the benefit of low temperature rise of the motor and longer battery life. As contact with bodily tissues is inherent to the device, the reduction in operating temperatures minimizes related trauma to surrounding body tissues. Red blood cell damage in blood pumps is mainly related to the shear stress and exposure time of the red blood cells passing through the flow paths. Higher shear stress regions in blood pumps usually occur in the blade tip gap regions, which are directly related to the pump speed. The two-stage impellers design requires a much lower pump speed than a purely single stage mixed-flow or axial flow blood pump in order to generate about 150 mmHg pressure rise for the need of a human body. The present invention, thus, provides a pump with low blood damage. The device further enables a pump to be provided in a small, compact size with the two-stage design as compared with the purely single stage mixed-flow (centrifugal) or single axial-flow type.

BRIEF DESCRIPTION OF THE DRAWINGS

The foregoing and other advantages of the invention will become apparent upon reading the following detailed description and upon reference to the drawings in which:

FIG. 10 is a perspective view of a component of the pump shown in FIG. 9;

FIG. 11 is an end view of the component shown in FIG. 10; and

DETAILED DESCRIPTION OF THE INVENTION

Embodiments are described more fully below in sufficient detail to enable those skilled in the art to practice the system and method. However, embodiments may be implemented in many different forms and the present invention should not be construed as being limited to the embodiments set forth herein. The following detailed description is, therefore, not to be taken to be limiting in any sense. For purpose of illustration, discussions of the technology will be made in reference to its utility as a cardiac assist blood pump. However, it is to be understood that the technology may have a variety of wide applications to many types of turbomachinery including, for example, commercial and industrial pumps, compressors, and turbines.

Figure 1:
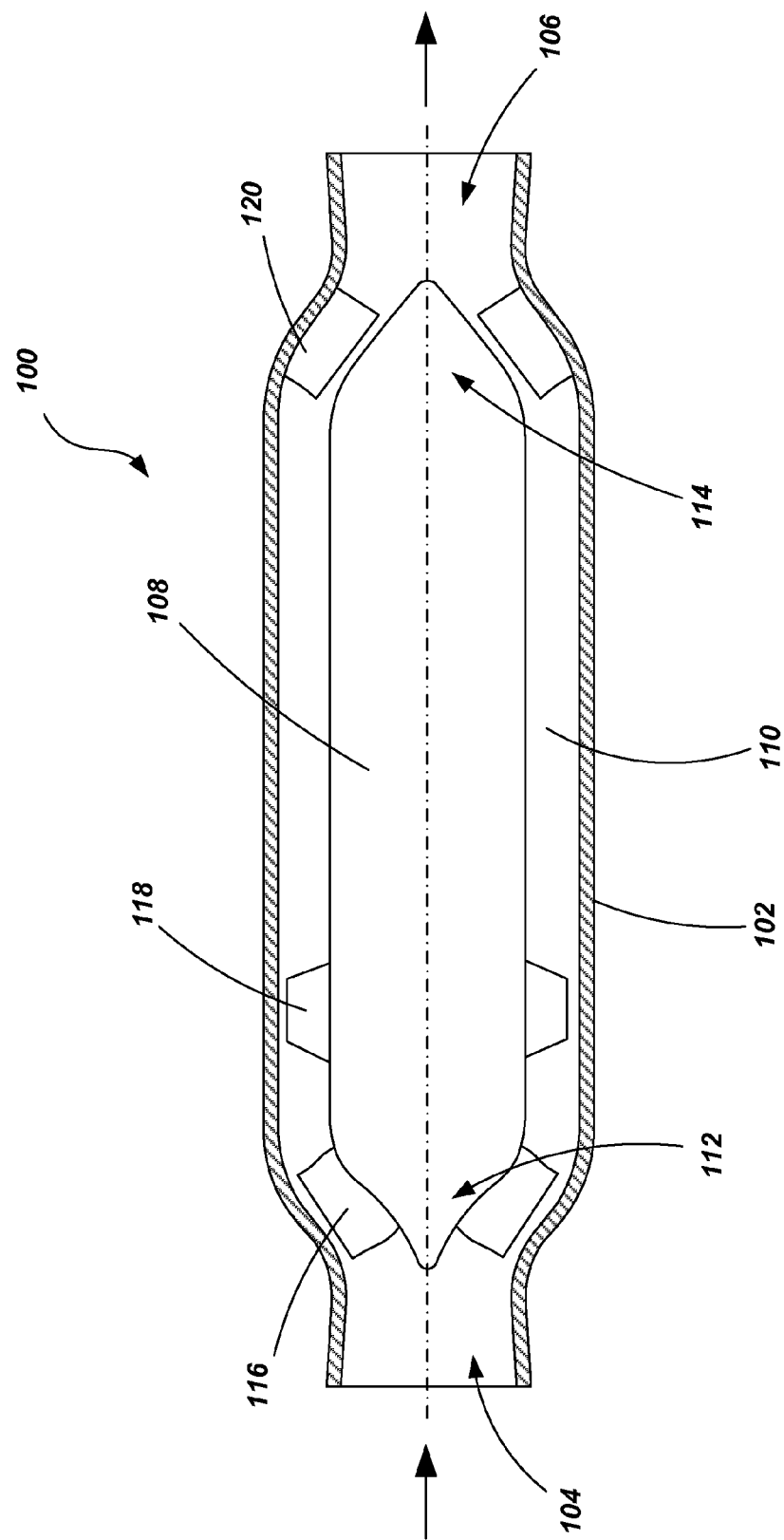
FIG. 1 is a longitudinal cross-sectional (meridional) view of a pump in accordance with an embodiment of the present invention.
Figure 2:
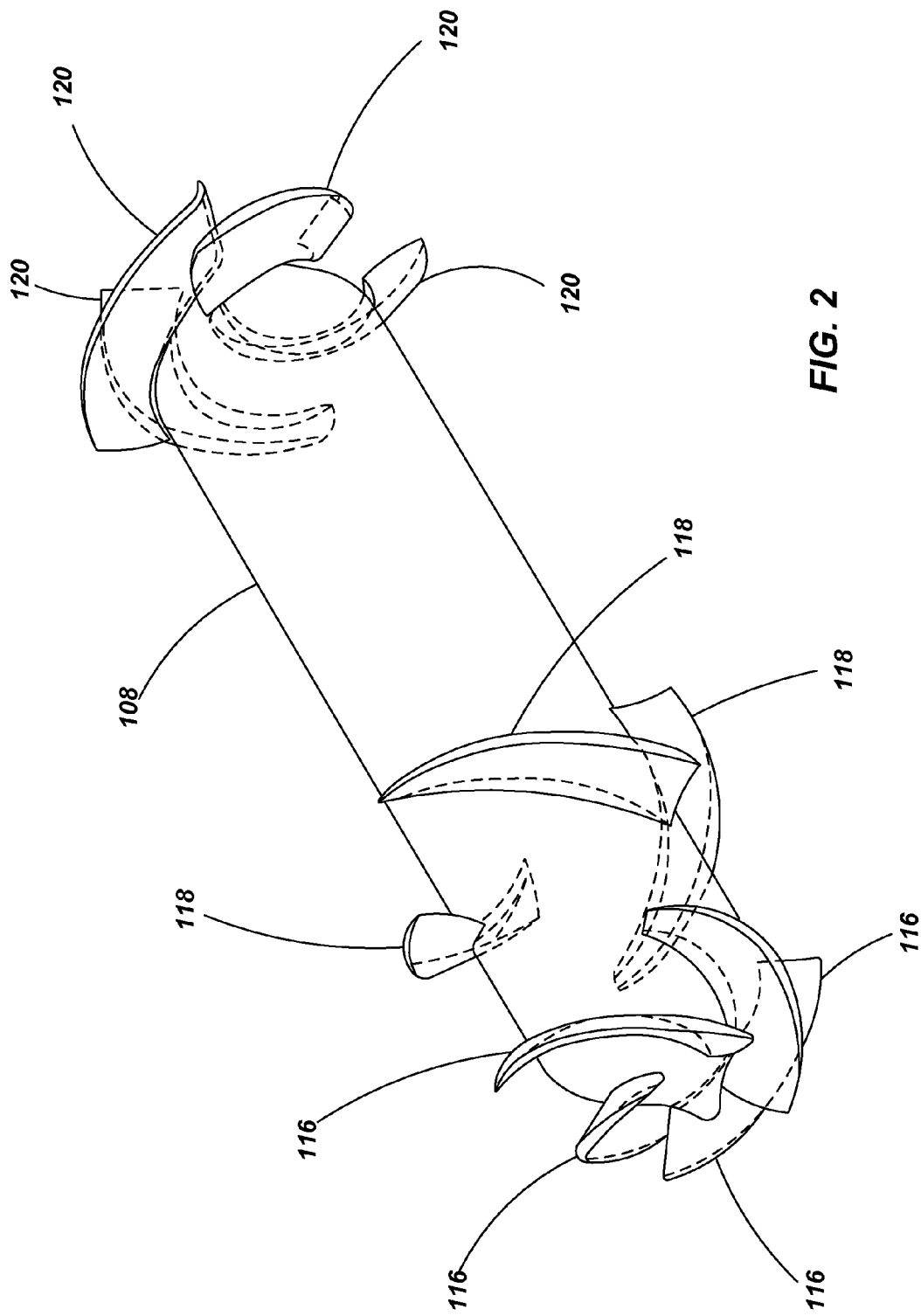
FIG. 2 is a perspective view of various components of the pump shown in FIG. 1.
Figure 3:
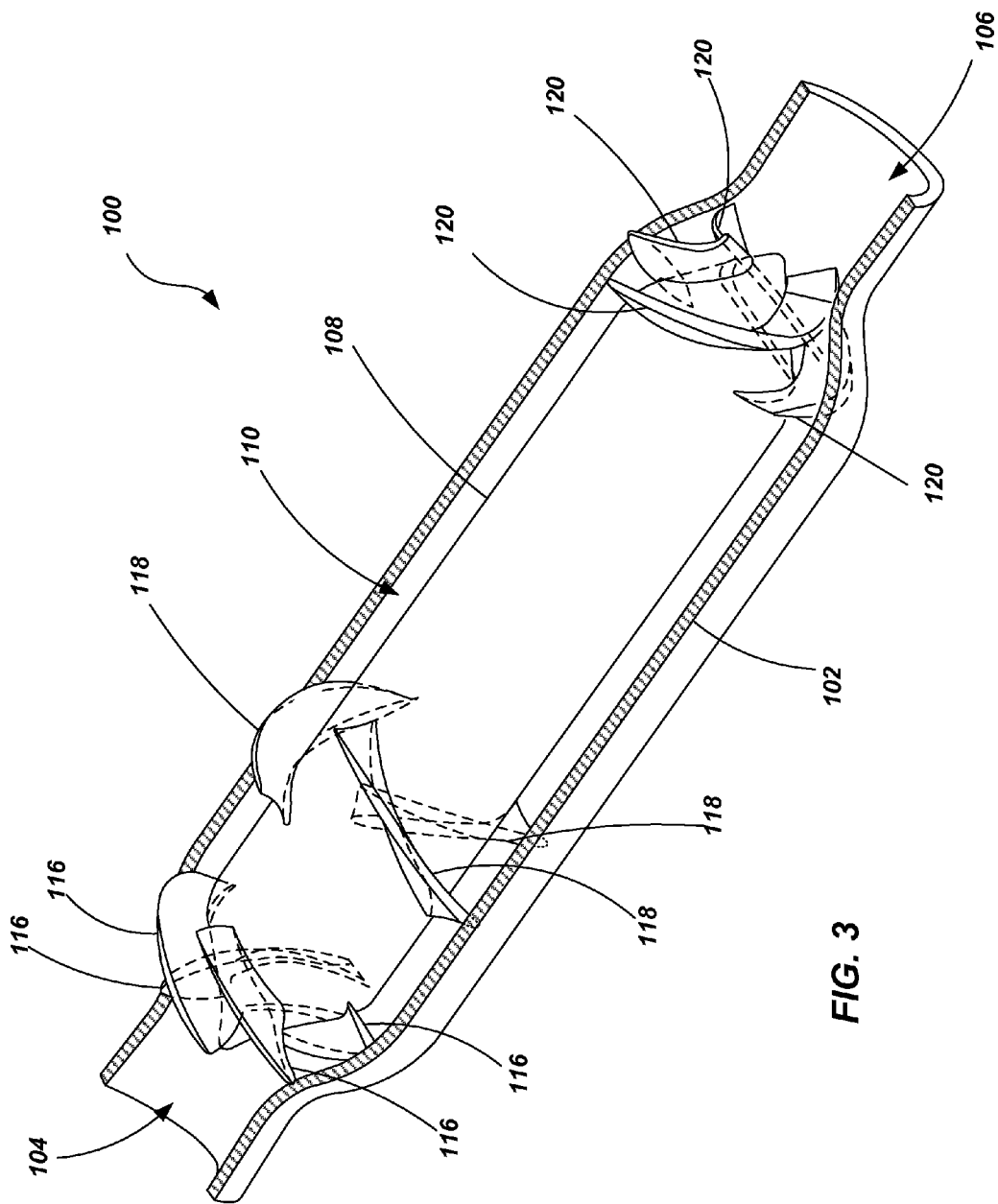
FIG. 3 is perspective view of various components of the pump shown in FIG. 1 including with a partial cross-sectional view of a housing member.

Referring to FIGS. 1 through 3, a rotordynamic blood pump 100 is shown in accordance with an embodiment of the present invention. FIG. 1 shows a meridional section of the pump 100. FIG. 2 shows a perspective view of various components of the pump, the housing of the pump being removed from the view for purposes of clarity. FIG. 3 shows a perspective view of the pump 100 with the housing being sectioned to provide context to other components of the pump 100.

The pump 100 includes a stator housing 102 having an inlet 104 and an outlet 106. A rotor hub 108 having a generally cylindrical configuration is disposed within an interior volume defined by the housing such that an annulus 110 or annular gap exists between the rotor hub 108 and the stator housing 102. The rotor hub 108 includes a leading portion 112 (i.e., leading with respect to intended fluid flow through the pump 100) that exhibits a generally conical geometry and that is positioned near the inlet 104. Additionally, the rotor hub 108 includes a trailing portion 112 (i.e., trailing with respect to intended fluid flow through the pump 100) that exhibits a generally conical geometry and that is positioned near the outlet 106.

The blood pump 100 is configured with multiple stages including a first, mixed-flow (or high-specific speed centrifugal) stage and a second, axial-flow stage. The impeller blades 116 associated with the first, mixed-flow stage are formed on, or otherwise coupled with, the rotor hub 108 along the leading portion 112 (i.e., in the conical region). The impeller blades 118 associated with the second, axial-flow stage are formed on, or otherwise coupled with, the rotor hub 108 at a location between the leading portion 112 and the trailing portion 114 such that they are disposed within the annulus 110 between the rotor hub 108 and the stator housing 102.

The first stage impeller blades 116 are positioned within in the inlet 104 of the stator housing 102, providing suction to the fluid entering the inlet 104 and delivering the fluid in both an axial and a radial direction. In the embodiment shown in FIG. 1, the second stage impeller blades 118 are located generally adjacent to the trailing edge of first stage impeller blades 116. However, as will be discussed in more detail below, the second stage impeller blades 116 may be positioned at other locations within the annulus 110. In the embodiment shown in FIG. 1, both stages are unshrouded. An unshrouded configuration may provide savings in cost and also reduce the complexity of manufacturing such a pump. However, in other embodiments shrouds may be incorporated into the impeller designs as will be discussed in further detail below. In an unshrouded configuration, a gap or clearance is maintained between lengthwise upper surface of the rotating impeller blades and the stationary stator housing.

Downstream of the first and second impeller blades 116 and 118, adjacent the pump outlet 106 and the trailing portion 114 of the rotor hub 108, a plurality of stator vanes 120 extend from an inner surface of the stator housing 102. The stator vanes 120 help to recover kinetic energy of the fluid (e.g., blood) and lead the fluid to flow axially through the outlet 106. A gap or clearance exists between the lengthwise lower surface of the stator vanes 120 and the rotor hub 108. The extent of both blade tip clearances and the vane tip clearances can have significant effects on the pump's performance including, for example, pump head and efficiency. Additionally, these clearances can have a significant impact on the amount of damage that may occur to the blood cells. In one particular embodiment, both the impeller blade tip clearances and the stator vane tip clearances may be approximately 0.1 mm to approximately 0.2 mm. However, the clearances may be set at other distances depending on a variety of factors as will be appreciated by those of ordinary skill in the art.

During operation of the pump, fluid enters through the inlet 104 of the pump 100 and encounters the first-stage impeller blades 116. The pressure of the fluid is raised by the first-stage impeller blades 116 and directed both radially outward and axially forward into the annulus 110 between the stator housing 102 and the rotor hub 108. The fluid then encounters the second-stage impeller blades 118 which further raises the pressure of the fluid and further axially displaces the fluid through the annulus 110. The fluid flows through the annulus 110 and encounters the stator vanes 120 prior to reaching the outlet 106 of the pump 100. The stator vanes 120 capture some of the kinetic energy of the fluid and direct the fluid in more of an axial direction. The stator vanes 120 also help to reduce turbulence that might develop during transition of the flow from the annulus 110 through the outlet 106.

It is noted that both the radial clearance and the axial length of the annulus 110 or annular gap can have a significant effect on pump performance and possible blood damage. For a magnetically suspended and rotated blood pump, the sizing of the annulus 110 also has an effect on the radial and yaw stiffness of the suspension system. From a point view of hydrodynamics, the radial gap of the annulus 110 should be made as large as reasonable possible, while for the consideration of magnetic suspension system, the radial gap of the annulus 110 should be small enough, and the axial length of the annulus 110 should long enough, to maintain a stable rotation of the rotor hub 106 within the stator housing 102. Improper design of such components, including the size of the annulus and the flow characteristics of the fluid passing through the annulus can lead to the rotor hub 106 being unstable and exhibiting, for example, a whip phenomenon as it rotates within the stator housing 102 when configured as a magnetic levitated pump.

It is noted that the components of the pump 100 are shown in relatively simplistic forms for sake of clarity in the associated description. For example, the magnetic and electronic components that might be utilized in association with a magnetic levitated pump are not specifically shown. However, one of ordinary skill in the art will recognize that such components will be inherently placed in or adjacent to the stator housing 102 and within the rotor hub 108 to provide such a magnetically levitated and rotated pump. One example of a completely magnetically suspended system associated with a pump is described in U.S. Patent Application Publication No. 20110237863 entitled MAGNETICALLY LEVITATED BLOOD PUMP WITH OPTIMIZATION METHOD ENABLING MINIATURIZATION, the disclosure of which is incorporated by reference herein in its entirety.

Still referring to FIGS. 1-3, it is seen that the pump may include four (4) first-stage impeller blades 116 of mixed-flow type, three (3) second-stage impeller blades 118 of axial-flow type, and four stator vanes 120. Of course, it is contemplated that other arrangements having more or fewer impeller blades 116 and 118 or stator vanes 120 may be utilized. The first stage and second stage impeller blades 116 and 118, as well as the stator vanes 120, all have 3-dimensional curved surfaces which can be designed, for example, using conventional turbomachinery inverse design theory such as 2D or quasi-3D methods. Their shapes and numbers may also be optimized via computational fluid dynamics (CFD) to reach the highest efficiency with minimal blood damage. The mixed-flow first-stage impeller blades 116 and the axial-flow second-stage impeller blades 118 may be designed, with respect to the head, such that the first stage provides approximately 50% to approximately 70% of the total pump head, while the second stage may provide approximately 30% to approximately 50% of the total pump head.

The leading edge angle of stage-two impeller blades 118 along each streamline may be set to be approximately equal to the trailing edge angle of the first-stage impeller blades 116 with a plus or minus attack angle of 0° to 5° by inverse design theory and CFD optimization so that the entrance flow matches well with the leading edge of the second stage impeller blades 118. The second stage blades 118 may be designed by aerofoil cascade theory together with CFD optimization to avoid complex and unreasonable very long blades. The blades of stator vanes 120 may be designed so that the leading edge angles generally match the flow out of the stage-two impeller blades 118. The trailing edge angles of the stator vanes 120 may be approximately 90° so that the blood or other fluid can be led to the outlet 106 substantially uniformly without minimal turbulence. The vane-to-vane sections and the meridional section part near the stator vanes 120 (as depicted in FIG. 1) may be designed and optimized by CFD so that they can further recover some potential energy (pressure) from the kinetic energy of the fluid flow.

In one particular embodiment, the pump 100 may be configured as an implantable blood pump wherein the rotor hub 108 is magnetically suspended and rotated. The rotor hub 108 may exhibit and overall length of approximately 106 mm and a diameter (exclusive of impeller blades 116 and 118) of approximately 12.4 mm. The inside diameter of the stator housing 102 may be approximately 16 mm, resulting in a clearance gap (for the annulus 110) of approximately 1.8 mm between rotor hub 108 and the inner surface of the stator housing 102. The inlet 104 and outlet 106 may each exhibit a diameter of approximately 8 mm. In such an embodiment, it has been calculated that blood entering the inlet 104 at a total pressure (i.e., kinetic pressure plus static pressure) of approximately 0 millimeters of mercury (mmHg), and at a flow rate of approximately 5 liters per minute (LPM) will experience a total increase of pressure of approximately 190-200 mmHg when it flows through the first-stage impeller blades 116 with the rotor hub 108 rotating at a speed of approximately 14,000 rotations per minute (RPM). The fluid will experience a further boost in pressure to a total pressure of between 240 and 250 mmHg (an increase of another approximately 50 mmHg over the first stage) as it flows through the second-stage impellers 118. Though the fluid experiences head loss as it flows through the remainder of the pump, the stator vanes 120 will help to capture kinetic energy and convert it into pressure while also directing the flow of the fluid in a more axial direction and minimizing turbulence such that the pressure of the fluid leaving the outlet 106 will be approximately 150 to 170 mmHg.

Of course, such an example is not to be considered limiting in any sense. The pump 100 may be configured to exhibit different dimensions, operate at different rotational speeds, and process fluid at different flow rates and pressures.

Figure 4:
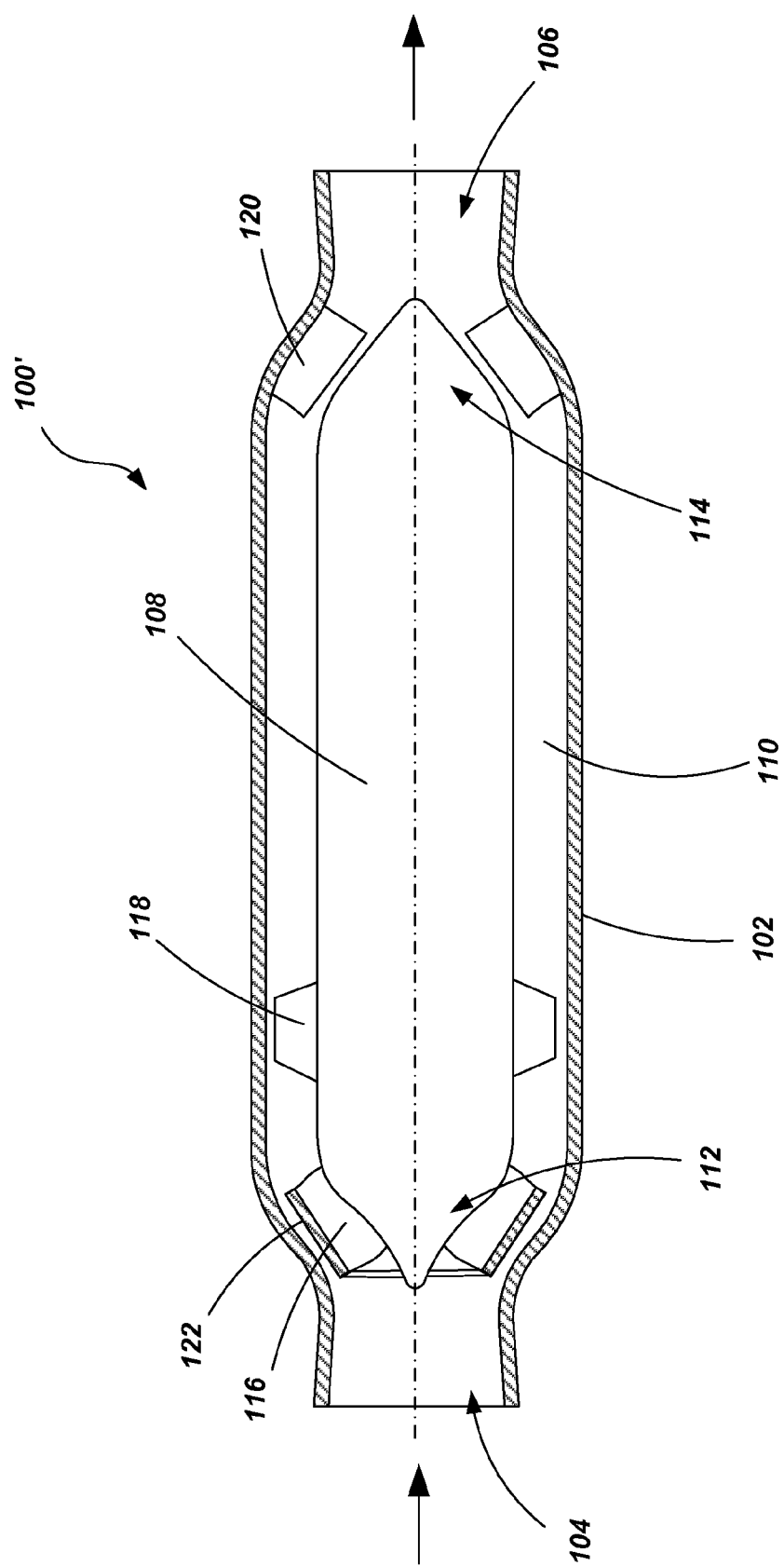
FIG. 4 is a longitudinal cross-sectional (meridional) view of a pump in accordance with another embodiment of the present invention.
Figure 5:
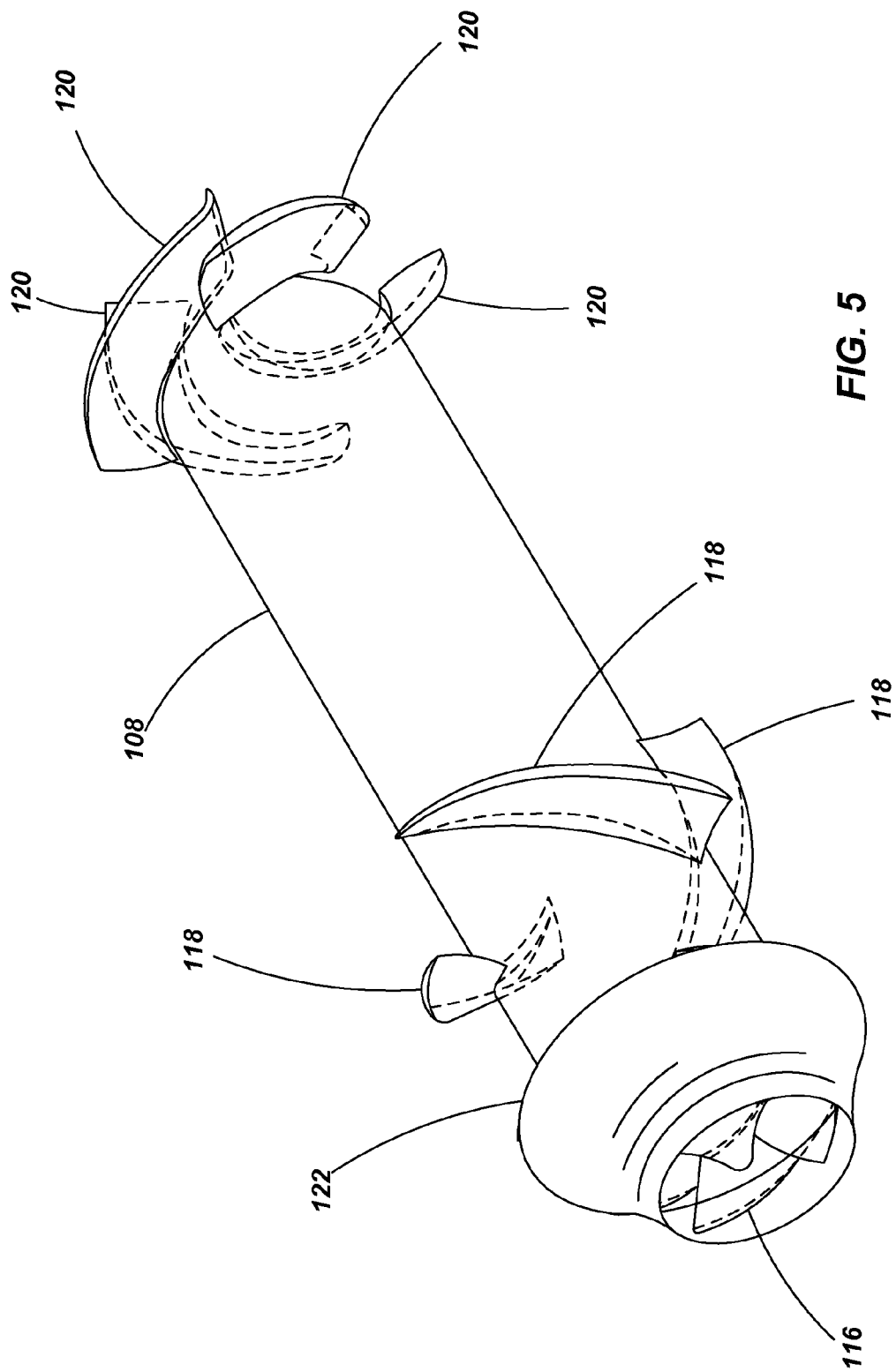
FIG. 5 is a perspective view of various components of the pump shown in FIG. 4.

Referring briefly to FIGS. 4 and 5, a pump 100' is shown in accordance with another embodiment of the present invention. The pump 100' is configured substantially similarly to that described above with respect to FIGS. 1-3. The pump 100' includes a stator housing 102 having an inlet 104 and an outlet 106. A rotor hub 108 having a generally cylindrical configuration is disposed within an interior volume defined by the housing such that an annulus 110 or annular gap exists between the rotor hub 108 and the stator housing 102. The rotor hub 108 includes a leading portion 112 that exhibits a generally conical geometry and that is positioned near the inlet 104. Additionally, the rotor hub 108 includes a trailing portion 112 that exhibits a generally conical geometry and that is positioned near the outlet 106. The pump 100' further includes impeller blades 116 associated with a first, mixed-flow stage, that are formed on, or otherwise coupled with, the rotor hub 108 along the leading portion 112 (i.e., in the conical region). Additionally, impeller blades 118 associated with a second, axial-flow stage, are formed on, or otherwise coupled with, the rotor hub 108 at a location between the leading portion 112 and the trailing portion 114 such that they are disposed within the annulus 110 between the rotor hub 108 and the stator housing 102. Downstream of the first and second impeller blades 116 and 118, adjacent the pump outlet 106 and the trailing portion 114 of the rotor hub 108, a plurality of stator vanes 120 extend from an inner surface of the stator housing 102.

The difference from the embodiment described with respect to FIGS. 1-3 is the inclusion of a front shroud 122 associated with the first stage impellers 116. The shroud 122 includes a solid surface that circumferentially encloses the radially outer ends of the first-stage impeller blades 116. A clearance gap is defined between the radial outer surface of the shroud 122 and the inner surface of the stator housing 102. An advantage of the shrouded blades is the elimination of blade tip leakage and the corresponding hydraulic losses that occur in an unshrouded configuration. The inclusion of a front shroud can also increase the mechanical strength of the impeller and may act as a damping touchdown for the magnetically suspended and rotated rotor hub 108. However, the use of shrouded blades can induce disk friction losses with a very complex retrograde flow pattern, possibly increasing the risk of blood damage. The use of a front shroud 122 may also increase the complexity and cost of the manufacturing, especially for systems comprising mixed-flow type impeller blades that are of miniature size.

Figure 6:
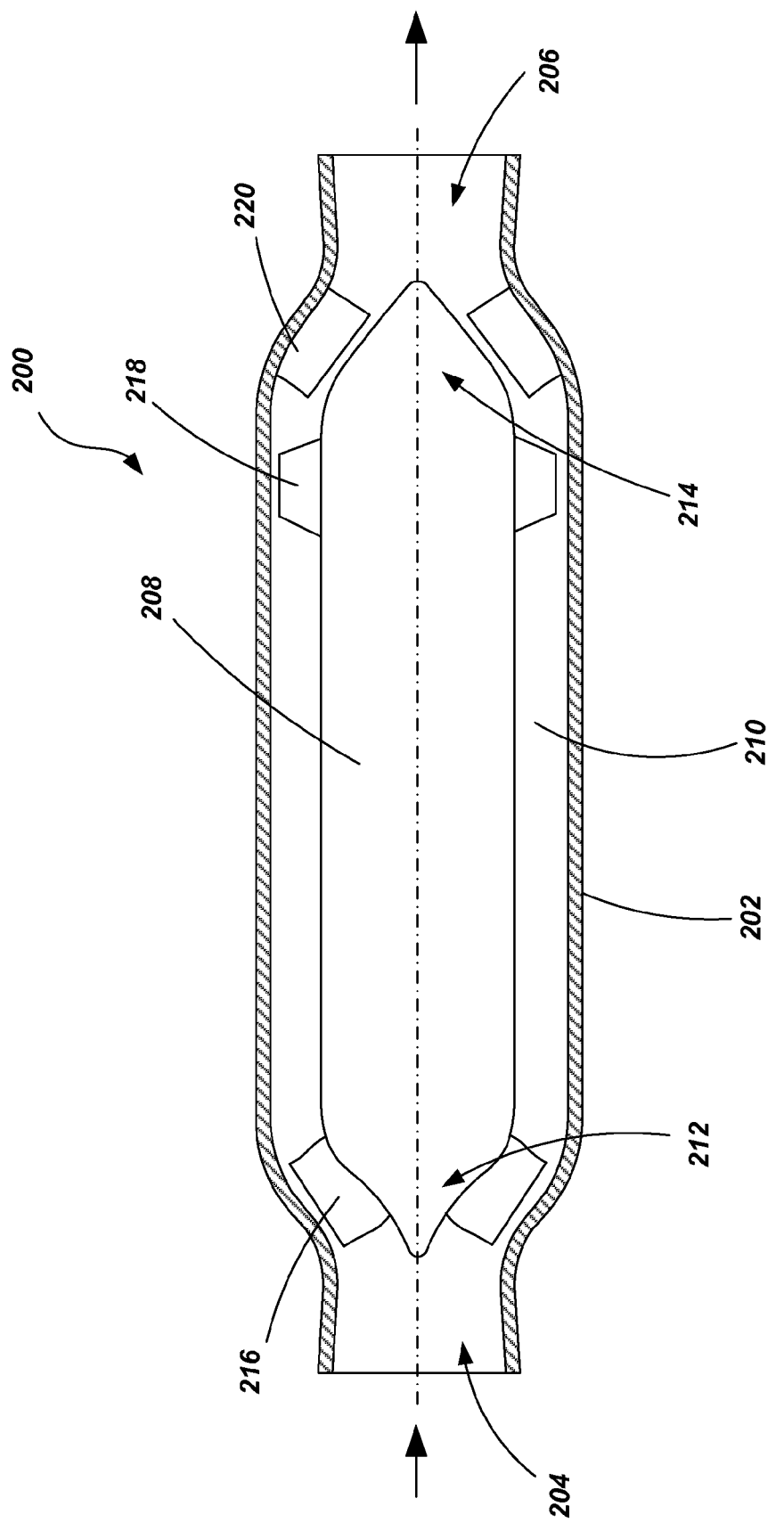
FIG. 6 is a longitudinal cross-sectional (meridional) view of a pump in accordance with another embodiment of the present invention.

Referring now to FIG. 6, another pump 200 is shown in accordance with yet another embodiment of the present invention. The pump 200 includes a stator housing 202 having an inlet 204 and an outlet 206. A rotor hub 208 having a generally cylindrical configuration is disposed within an interior volume defined by the housing such that an annulus 210 or annular gap exists between the rotor hub 208 and the stator housing 202. The rotor hub 208 includes a leading portion 212 that exhibits a generally conical geometry and that is positioned near the inlet 204. Additionally, the rotor hub 208 includes a trailing portion 212 that exhibits a generally conical geometry and that is positioned near the outlet 206. The pump 200 further includes impeller blades 216 associated with a first, mixed-flow stage, that are formed on, or otherwise coupled with, the rotor hub 208 along the leading portion 212 (i.e., in the conical region). Additionally, impeller blades 218 associated with a second, axial-flow stage, are formed on, or otherwise coupled with, the rotor hub 208 at a location between the leading portion 212 and the trailing portion 214 such that they are disposed within the annulus 210 between the rotor hub 208 and the stator housing 202. Downstream of the first and second impeller blades 216 and 218, adjacent the pump outlet 206 and the trailing portion 214 of the rotor hub 208, a plurality of stator vanes 220 extend from an inner surface of the stator housing 202.

It is noted that the second-stage impeller blades are positioned downstream within the annulus 210 nearer to the stator vanes 220 than to the first-stage impeller blades 216. This is in distinction to the embodiment described with respect to FIGS. 1-3 (wherein the second-stage impeller blades 118 are positioned closer to the first-stage impeller blades 116 than they are to the stator vanes 120). Stated another way, the second-stage impeller blades 218 are positioned nearer to trailing portion 214 of the rotor hub 208 than to the leading portion 212 of the rotor hub 208 (and nearer to the inlet 204 than to the outlet 206). The positioning of the second-stage impeller blades 218 nearer to the trailing portion 214 may provide greater stabilization to the rotor hub 208 during operation of the pump 200 so as to minimize or prevent any whip phenomenon that might occur. For example, because of the increase in circumferential velocity of the fluid imposed by the second-stage impellers, when the second-stage impellers 218 are positioned nearer to the leading portion of the rotor hub, the rotor hub, under certain operating conditions, may experience a whip phenomenon and exhibits signs of instability. In the embodiment shown in FIG. 6, the second-stage impeller blades 218 can boost the pressure and flow rate (as with the configuration described with respect to FIGS. 1-3) while providing increased stability because the increased circumferential velocity imparted by the second-stage impeller blades 218 will be converted, nearly immediately, into pressure by the stator vanes 220 and the circumferential velocity will be significantly reduced, to nearly zero, as the fluid flows out from the stator vanes 220.

Figure 7:
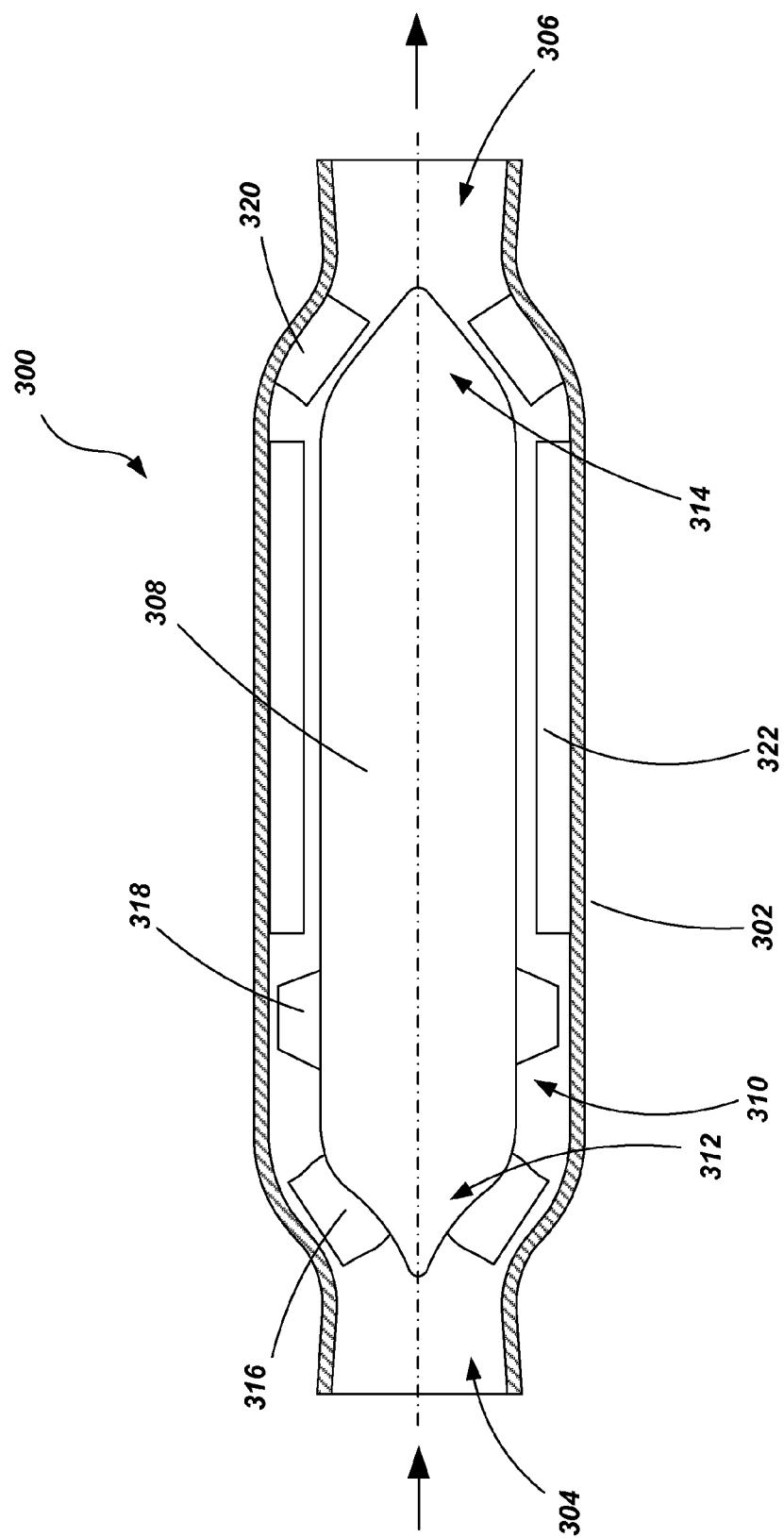
FIG. 7 is a longitudinal cross-sectional (meridional) view of a pump in accordance with further embodiment of the present invention.

Referring now to FIG. 7, a pump 300 is shown in accordance with a further embodiment of the present invention. The pump 300 includes a stator housing 302 having an inlet 304 and an outlet 306. A rotor hub 308 having a generally cylindrical configuration is disposed within an interior volume defined by the housing such that an annulus 310 or annular gap exists between the rotor hub 308 and the stator housing 302. The rotor hub 308 includes a leading portion 312 that exhibits a generally conical geometry and that is positioned near the inlet 304. Additionally, the rotor hub 308 includes a trailing portion 312 that exhibits a generally conical geometry and that is positioned near the outlet 306. The pump 300 further includes impeller blades 316 associated with a first, mixed-flow stage, that are formed on, or otherwise coupled with, the rotor hub 308 along the leading portion 312 (i.e., in the conical region). Additionally, impeller blades 318 associated with a second, axial-flow stage, are formed on, or otherwise coupled with, the rotor hub 308 at a location between the leading portion 312 and the trailing portion 314 such that they are disposed within the annulus 310 between the rotor hub 308 and the stator housing 302. Downstream of the first and second impeller blades 316 and 318, adjacent the pump outlet 306 and the trailing portion 314 of the rotor hub 308, a plurality of stator vanes 320 extend radially inward from the stator housing 302.

The pump 300 additionally includes annular stator vanes 322 within the annulus 310 extending radially inward from the stator housing 302 and being axially positioned between the leading and trailing portions of the rotor hub 308 (312 and 314). A clearance gap is formed between the annular stator vanes 322 and the rotor hub 308. In this particular embodiment, the annular stator vanes 322 are positioned between the second-stage impellers 318 and the stator vanes 320 are positioned in the converging portion of the stator housing 302 (i.e., adjacent the trailing portion of the rotor hub 314 and the outlet 306). As seen in FIG. 7, the annular stator vanes 322 may extend a substantial length, even substantially filling the axial distance between the second-stage impellers 318 and the stator vanes 320 near the outlet 306. Of course, the annular stator vanes 322 may be configured to extend a shorter axial distance through the annulus 310.

In the embodiment shown in FIG. 7, the annular stator vane 322 can reduce or eliminate the flow circulation induced by the second-stage impeller blades 318 to help prevent fluid instability while recovering some of the pressure from the kinetic energy of the fluid flow.

Figure 8:
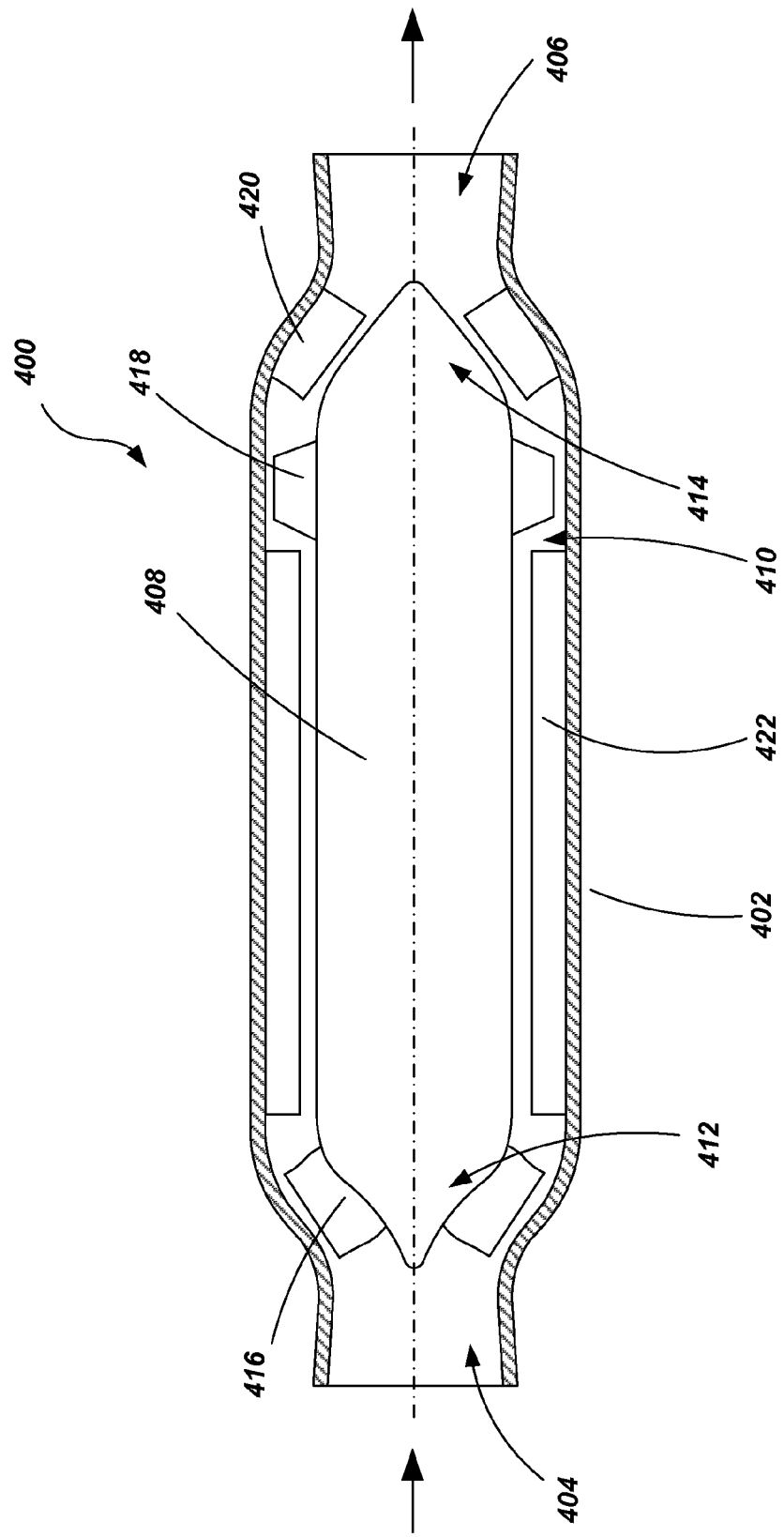
FIG. 8 is a longitudinal cross-sectional (meridional) view of a pump in accordance with yet another embodiment of the present invention.
Figure 9:
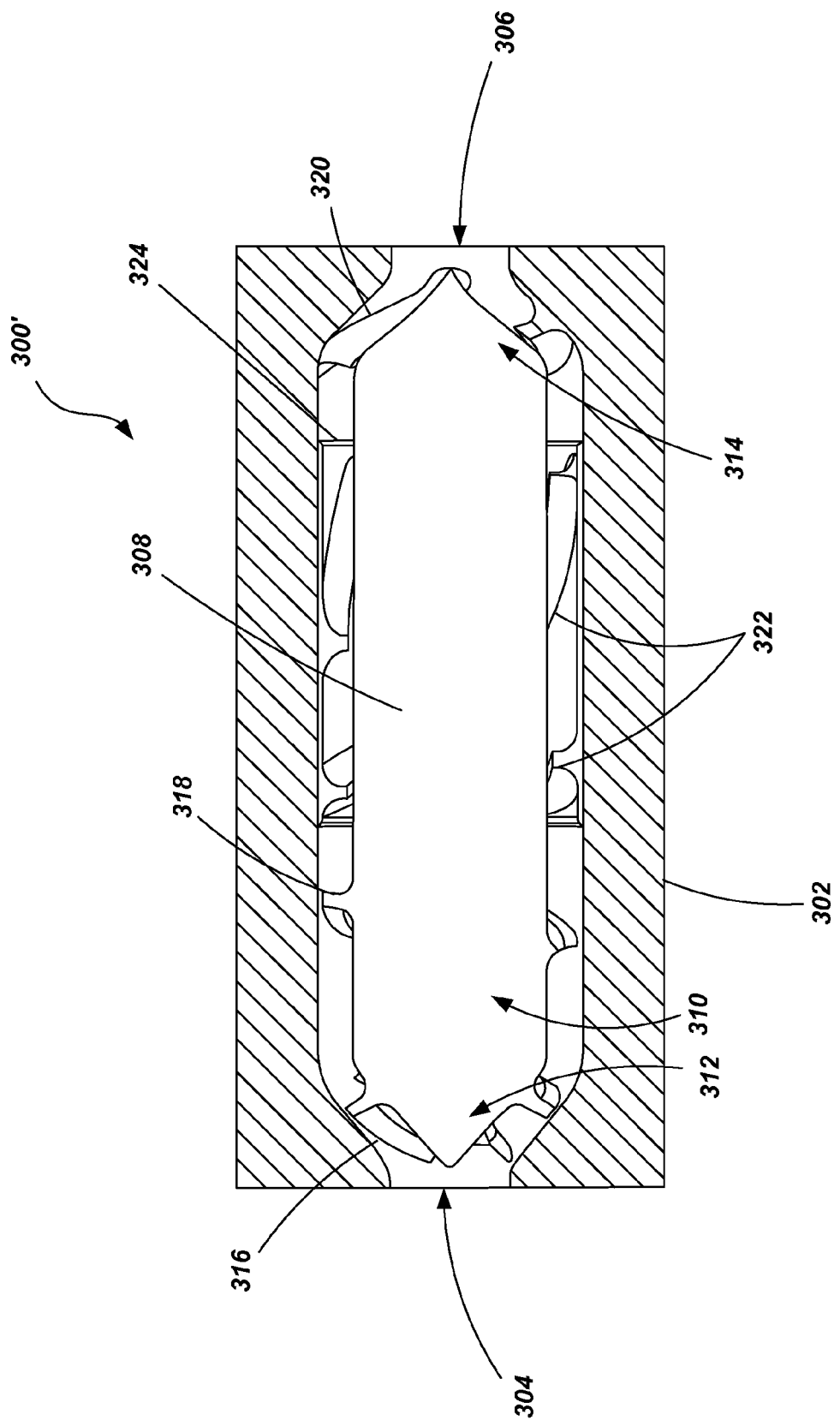
FIG. 9 is a longitudinal cross-sectional (meridional) view of a pump in accordance with another embodiment of the present invention.
Figure 12:
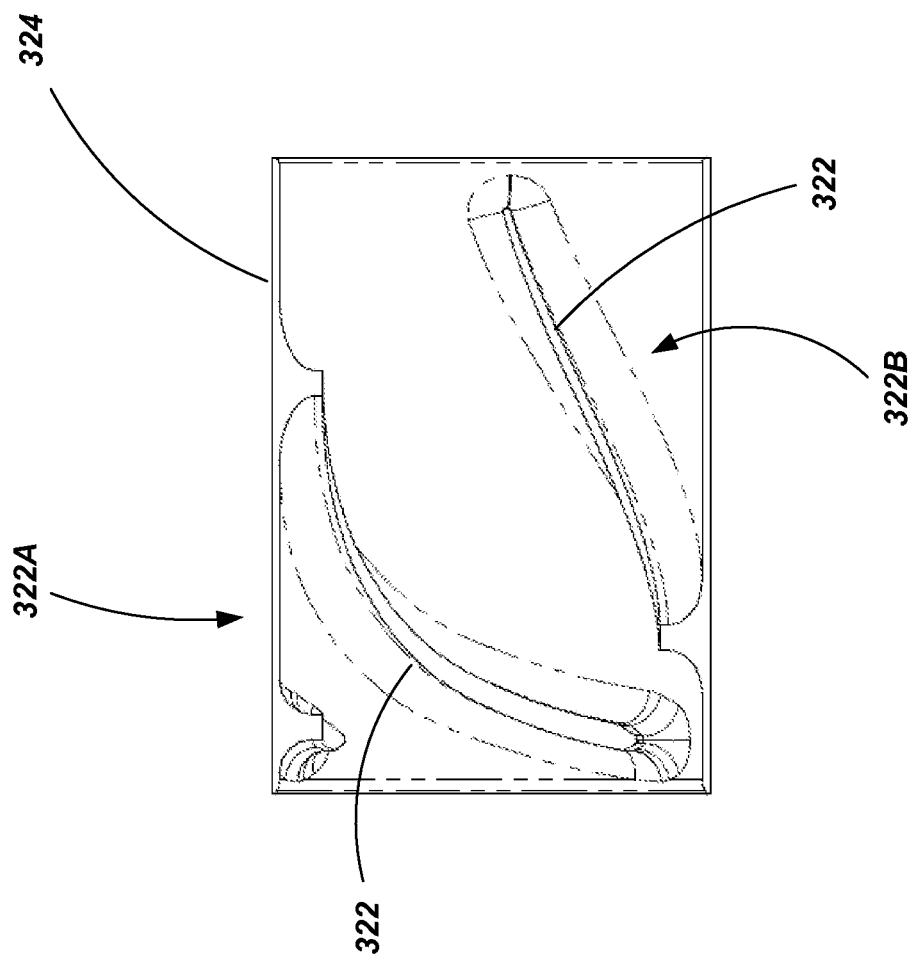
FIG. 12 is partial cross-sectional view of the component shown in FIG. 10.

Referring now to FIG. 8, a pump 400 is shown in accordance with yet a further embodiment. The pump 400 includes a stator housing 402 having an inlet 404 and an outlet 406. A rotor hub 408 having a generally cylindrical configuration is disposed within an interior volume defined by the housing such that an annulus 410 or annular gap exists between the rotor hub 408 and the stator housing 402. The rotor hub 408 includes a leading portion 412 that exhibits a generally conical geometry and that is positioned near the inlet 404. Additionally, the rotor hub 408 includes a trailing portion 412 that exhibits a generally conical geometry and that is positioned near the outlet 406. The pump 400 further includes impeller blades 416 associated with a first, mixed-flow stage, that are formed on, or otherwise coupled with, the rotor hub 408 along the leading portion 412 (i.e., in the conical region). Additionally, impeller blades 418 associated with a second, axial-flow stage, are formed on, or otherwise coupled with, the rotor hub 408 at a location between the leading portion 412 and the trailing portion 414 such that they are disposed within the annulus 410 between the rotor hub 408 and the stator housing 402. Downstream of the first and second impeller blades 416 and 418, adjacent the pump outlet 406 and the trailing portion 414 of the rotor hub 408, a plurality of stator vanes 420 extend radially inward from the stator housing 402.

It is noted that the second-stage impeller blades are positioned downstream within the annulus 410 nearer to trailing portion 414 of the rotor hub 408 than to the leading portion 412 of the rotor hub 408 (and nearer to the outlet 406 than to the inlet 406, similar to the embodiment described with respect to FIG. 6).

The pump additionally includes annular stator vanes 422 positioned between the leading and trailing portions of the rotor hub 408 (412 and 414) within the annulus 410 extending radially inward from the stator housing 402. A clearance gap is formed between the annular stator vanes 422 and the rotor hub 408. In this particular embodiment, the annular stator vanes 422 are positioned between the first-stage impeller blades 416 and the second-stage impellers 418. As seen in FIG. 8, the annular stator vanes 422 may extend a substantial length, even substantially filling the axial distance between the first-stage impeller blades 416 and the second-stage impeller blades 418. Of course, the annular stator vanes may be configured to extend a shorter axial distance through the annulus 410.

In this configuration, the annular stator vanes 422 can immediately reduce and eliminate the circumferential velocity of the fluid out of the first-stage impeller blades 416, thus recovering the pressure and increasing the operational stability of the rotor hub 408. Because the flow enters the second-stage impeller blades 418 without circulation, or with only little circulation, the hydraulic loss within the second-stage impeller region can be significantly reduced. Thus the total pump efficiency can be increased.

Referring now to FIGS. 9-12, a pump 300' and its associated components are shown in accordance with another embodiment of the present invention. The pump 300' is substantially similar to pump 300' described with respect to FIG. 7 hereinabove. Generally, the pump 300' includes a stator housing 302 having an inlet 304 and an outlet 306 and a rotor hub 308 having a generally cylindrical configuration disposed within an interior volume defined by the housing such that an annulus 310 or annular gap exists between the rotor hub 308 and the stator housing 302. The rotor hub 308 includes a leading portion 312 that exhibits a generally conical geometry and that is positioned near the inlet 304. Additionally, the rotor hub 308 includes a trailing portion 312 that exhibits a generally conical geometry and that is positioned near the outlet 306. The pump 300' further includes impeller blades 316 associated with a first, mixed-flow stage, that are formed on, or otherwise coupled with, the rotor hub 308 along the leading portion 312 (i.e., in the conical region). Additionally, impeller blades 318 associated with a second, axial-flow stage, are formed on, or otherwise coupled with, the rotor hub 308 at a location between the leading portion 312 and the trailing portion 314 such that they are disposed within the annulus 310 between the rotor hub 308 and the stator housing 302. Downstream of the first and second impeller blades 316 and 318, adjacent the pump outlet 306 and the trailing portion 314 of the rotor hub 308, a plurality of stator vanes 320 extend radially inward from the stator housing 302. The pump additionally includes annular stator vanes 322 positioned between the leading and trailing portions of the rotor hub 308 (312 and 314) within the annulus 310 extending radially inward from the stator housing 302.

The annular stator vanes 322 are configured as an insert 324 to be positioned within the stator housing 302 between the interior surface of the stator housing 302 and the rotor hub 308. The use of an insert 324 to provide annular stator vanes 322 within the stator housing 302 provides flexibility in manufacturing the pump. For example, while one way of manufacturing the stator housing may include the formation of a "split" housing (i.e., split lengthwise axially), such a configuration may cause issues with flow dynamics of fluid passing therethrough. Additionally, while various manufacturing techniques may be used to form the stator housing to provide a substantially monolithic, homogenous surface exposed to the fluid during pump operation, the manufacturing techniques to do so can be expensive and time consuming. Thus, use of an insert may be a relatively inexpensive way to overcome such challenges. Additionally, as seen in FIGS. 9-12, multiple stages of annular stator vanes 322 may be implemented, with a first stage 322A having a first angular disposition relative to the axial length of the pump 300', and a second stage 322B having a second, different angular disposition relative to the axial length of the pump 300'. Such a configuration provides greater control of the fluid flow so as to provide a desired pressure increase without turbulence or other instability within the system.

Manufacturing of the insert (or the stator housing, when stator vanes are integral therewith) may be accomplished using a variety of techniques. For example, an annular insert 324 may be formed using computer numerically controlled (CNC) milling, electro-discharge machine (EDM) milling, and casting.

In various instances, such as when implemented in a "miniature" embodiment of the invention, it might not be feasible (or it may at least be extremely difficult) to fabricate the inward pointing blades of the stator vanes within the confined tubular structure using conventional technology such as milling, electric discharge machining or molding. However additive rapid manufacturing technologies may be used to create such components as they are capable of manufacturing metal components comprising complex geometries.

One such rapid-manufacturing technology is known as direct metal laser sintering (DMLS) and can build solid metal parts directly from powdered metals in a manner that can compliment or even replace traditional machining DMLS provides a wide range of part properties, from controlled porosity for venting or filtering to fully dense structures with a higher strength than castings and forgings.

In one example of a DMLS process, a technician can import a scan or other 3D-CAD data into the process software to position and orient parts. After the operator selects a desired material, the software assigns correct building parameters and "slices" the 3D data into 2-dimensional layers. This data is then sent to a DMLS machine. The operator then fixes a steel plate inside the machine on which parts will be built. A dispenser in the machine applies raw powder one the plate and a coater arm having a blade spreads the powder as a 20 or 40-µm (8 or 16 micro-inch) layer on top of the plate. Machine software controls the position and focus of a laser beam such that it travels across a defined cross-section (or slice) of the part to be built. Wherever the beam strikes, it melts the powder into a solid, and melts the solid onto the metal below as well. This process continues, layer-by-layer, until the build completes. The steel plate acts as a heat sink so that the melted metal solidifies rapidly. For most materials, the build chamber is filled with an inert gas, such as nitrogen or argon, to protect parts from oxidation.

It is also noted that, depending on the manufacturing process being used, a finishing process (such as polishing) may be desired to provide final dimensions and surface specifications of the part. For example, if a rough process is used (such as casting or additive manufacturing with a DMLS technology or the like), features with tightly controlled tolerances such as the outside diameter and internal diameter of the blade tips can be post machined using conventional turning or milling techniques. The other inside surfaces can also be post machined using conventional milling or finishing techniques to result in more accurate surfaces with reduced roughness.

Challenges with polishing such a structure with deep pockets are similar to the challenge of manufacturing the unfinished structure. Deep crevices make it less feasible to utilize conventional hand polishing approaches. An annular insert comprising inward pointing blades is desirably finished using an automated mass finishing process in which chemical and/or abrasive means are employed to refine the interior surfaces. One such process, known as Isotropic Superfinish Process (ISF®) provided by REM Chemicals avoids abrasive machining to lap, grind and hone individual parts and mass finished components utilizing a non-abrasive technique for mass finishing which results in more efficient, uniform parts as compared to using an abrasive media. Such a process is described in U.S. Pat. No. 7,005,080, entitled NONABRASIVE MEDIA WITH ACCELERATED CHEMISTRY, the disclosure of which is incorporated by reference herein in its entirety. Other possible mass-finishing technologies include electro polishing, vibration-abrasive polishing, and Extrude Hone®.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims. It is specifically noted that any features or aspects of a given embodiment described above may be combined with any other features or aspects of other described embodiments, without limitation. Additionally, it is contemplated that the present invention may also incorporate one or more features or aspects of related U.S. patent application Ser. No. 13/276,009, entitled BLOOD PUMP WITH SPLITTER IMPELLER BLADES AND SPLITTER STATOR VANES AND RELATED METHODS, filed on even date herewith, the disclosure of which is incorporated by reference herein.

What is claimed is:

1. An implantable blood pump configured to provide continuous fluid flow, comprising:
   a stator housing having an inlet, an outlet downstream from the inlet, the stator housing defining a closed fluid pathway extending from the inlet to the outlet;
   a rotor having a rotor hub disposed within the fluid pathway, the rotor hub having a leading portion positioned adjacent the inlet, the leading portion having a diameter increasing with distance in the downstream direction, a trailing portion positioned adjacent the outlet, the trailing portion having a diameter decreasing with distance in the downstream direction, and a cylindrical intermediate portion extending from the leading portion to the trailing portion, the rotor having a mixed-flow first stage positioned at the leading portion comprising at least one first-stage impeller blade coupled with the leading portion, and a single axial-flow second stage positioned on the intermediate portion of the rotor hub in an annulus of the stator housing which surrounds the intermediate portion between the leading portion and the trailing portion, the single axial-flow second stage comprising at least one second-stage impeller blade coupled with the intermediate portion and positioned closer to the outlet than to the inlet, the at least one second-stage impeller blade having an impeller blade tip clearance with the annulus, the impeller blade tip clearance having an axial dimension in an axial direction of the pump; and
   components associated with the stator housing which, in operation of the pump, are configured to completely magnetically suspend the rotor hub and cause the rotor hub to rotate;
   at least one stator vane extending radially inward from the stator housing and positioned in the annulus such that a stator vane tip clearance is defined between the at least one stator vane and the rotor hub, the at least one stator vane substantially filling an axial distance between the at least one mixed flow first-stage impeller blade and the at least one second-stage impeller blade, the stator vane tip clearance having an axial dimension in the axial direction of the pump,
   wherein the pump is configured to increase fluid pressure downstream of the mixed flow first stage to a first pressure level and is configured to increase fluid pressure downstream of the axial-flow second stage to a second pressure level of about 50 mmHg greater than the first pressure level,
   and the pump is operable at the pump speed of approximately 14,000 rotations per minute (rpm) at a rotor hub diameter of 12 millimeters and the axial dimension of the axial-flow second stage impeller blade tip clearance is shorter than the axial dimension of the stator vane tip clearance.

2. The pump of claim 1, wherein the leading portion and the trailing portion each exhibit substantially conical geometries.

3. The pump of claim 2, wherein the at least one first stage impeller blade comprises a plurality of blades which are curved along a three-dimensional path along the leading portion of the rotor hub.

4. The pump of claim 3, further comprising a shroud connected to the plurality of blades.

5. The pump of claim 1, wherein the at least one second-stage impeller blade comprises a plurality of impeller blades which are curved along a three-dimensional path axially along the body of the rotor hub.

6. The pump of claim 1, wherein the at least one stator vane is integrally formed with the stator housing.

7. The pump of claim 1, wherein the at least one stator vane is formed on a tubular insert disposed within the stator housing.

8. The pump of claim 1, wherein the rotor hub and the stator housing are configured of blood compatible materials.

9. The pump as claimed in claim 1, wherein the stator vane tip clearance between the tip of the at least one stator vane and the intermediate portion of the rotor hub has a dimension from approximately 0.1 millimeters to approximately 0.2 millimeters.

10. The pump as claimed in claim 1, wherein a temperature rise of the pump during operation is minimized.

11. An implantable blood pump configured to provide continuous fluid flow, comprising:
    a stator housing having an inlet, an outlet downstream from the inlet, the stator housing defining a closed fluid pathway from the inlet to the outlet;
    a rotor having a rotor hub disposed within the fluid pathway, the rotor hub having a leading portion positioned adjacent the inlet, a trailing portion positioned adjacent the outlet, and a cylindrical intermediate portion extending from the leading portion to the trailing portion, wherein a width of the leading portion increases with distance in the downstream direction and a width of the trailing portion decreases with distance in the downstream direction, the rotor having a mixed-flow first stage positioned at the leading portion comprising at least one mixed flow first-stage impeller blade coupled with the leading portion, and a single axial-flow second stage positioned on the intermediate portion in an annulus of the stator housing which surrounds the intermediate portion between the leading and trailing portions of the rotor hub, the second stage closer to the outlet than to the inlet, the second stage comprising at least one second-stage impeller blade having an impeller blade tip clearance with the annulus, the impeller blade tip clearance having an axial dimension in an axial direction of the pump; and
    components associated with the stator housing which, in operation of the pump, are configured to completely magnetically suspend the rotor hub and cause the rotor hub to rotate; and
    at least one stator vane extending radially inward from the stator housing and positioned in the annulus such that a stator vane tip clearance is defined between the at least one stator vane and the rotor hub, the stator vane tip clearance having an axial dimension in the axial direction of the pump, the at least one stator vane substantially filling an axial distance in the annulus not occupied by the at least one second-stage impeller blade,
    wherein the pump is operable at a pump speed of approximately 14,000 rpm at a rotor hub diameter of 12 millimeters, and the axial dimension of the axial-flow second stage impeller blade tip clearance is shorter than the axial dimension of the stator vane tip clearance.

12. The pump as claimed in claim 11, wherein the pump is configured to increase fluid pressure downstream of the at least one mixed flow first-stage impeller blade to a first pressure level and is configured to increase fluid pressure downstream of the at least one second-stage impeller blade to a second pressure level greater than the first pressure level.

13. An implantable blood pump configured to provide continuous fluid flow, comprising:

a stator housing having an inlet, an outlet downstream from the inlet, the stator housing defining a closed fluid pathway extending from the inlet to the outlet;

a rotor having a rotor hub disposed within the fluid pathway, the rotor hub having a leading portion positioned adjacent the inlet, the leading portion having a diameter increasing with distance in the downstream direction, a trailing portion positioned adjacent the outlet, the trailing portion having a diameter decreasing with distance in the downstream direction, and having an intermediate portion extending from the leading portion to the trailing portion, the rotor having a mixed-flow first stage positioned at the leading portion comprising at least one first stage impeller blade coupled with the leading portion, and an axial-flow second stage positioned on the intermediate portion of the rotor hub in an annulus of the stator housing which surrounds the intermediate portion of the rotor hub between the leading and trailing portions, the axial-flow second stage comprising at least one second-stage impeller blade coupled with the intermediate portion and having an impeller blade tip clearance with the annulus, the impeller blade tip clearance having an axial dimension in an axial direction of the pump;

components associated with the stator housing which, in operation of the pump, are configured to completely magnetically suspend the rotor hub and cause the rotor hub to rotate; and at least one stator vane extending radially inward from the stator housing and positioned in the annulus such that a stator vane tip clearance is defined between the at least one stator vane and the rotor hub, the at least one stator vane substantially filling an axial distance in the annulus not occupied by the at least one second-stage impeller blade, the stator vane tip clearance having an axial dimension in the axial direction of the pump, wherein the pump is operable at a speed of approximately 14,000 rpm and a rotor hub diameter of 12 millimeters, and the axial dimension of the impeller blade tip clearance of the at least one second-stage impeller blade is shorter than the axial dimension of the stator vane tip clearance.

14. The pump as claimed in claim 13, wherein the pump is configured to increase fluid pressure downstream of the at least one mixed flow first-stage impeller blade to a first pressure level and is configured to increase fluid pressure downstream of the at least one second-stage impeller blade to a second pressure level of about 50 mmHg greater than the first pressure level.

15. An implantable blood pump configured to provide continuous fluid flow, comprising:

a stator housing having an inlet, an outlet downstream from the inlet, the stator housing defining a closed fluid pathway from the inlet to the outlet;

a rotor having a rotor hub disposed within the fluid pathway, the rotor hub having a leading portion positioned adjacent the inlet, a trailing portion positioned adjacent the outlet, and a cylindrical intermediate portion extending from the leading portion to the trailing portion, wherein a width of the leading portion increases with distance in the downstream direction and a width of the trailing portion decreases with distance in the downstream direction, the rotor having a mixed-flow first stage positioned on the leading portion comprising at least one mixed flow first-stage impeller blade coupled with the leading portion, and an axial-flow second stage being the only impeller stage positioned on the intermediate portion, the axial flow second stage positioned at one of: closer to the inlet than to the outlet, or closer to the outlet than the inlet, the second stage comprising at least one second-stage impeller blade having an impeller blade tip clearance with the annulus, the impeller blade tip clearance having an axial dimension in an axial direction of the pump; and components associated with the stator housing which, in operation of the pump, are configured to completely magnetically suspend the rotor hub and cause the rotor hub to rotate; and at least one stator vane extending radially inward from a converging portion of the stator housing surrounding the trailing portion of the rotor hub, the at least one stator vane having a stator vane tip clearance defined between the at least one stator vane and the rotor hub, the stator vane tip clearance having an axial dimension, wherein the pump is operable at a pump speed of approximately 14,000 rpm at a rotor hub diameter of 12 millimeters and the axial dimension of the impeller blade tip clearance of the axial flow second stage is reduced in relation to the axial dimension of the stator vane tip clearance.

* * * * *